United States Patent
Draper (10) Patent No.: US 9,943,336 B2
(45) Date of Patent: Apr. 17, 2018

(54) BONE FIXATED, ARTICULATED JOINT LOAD CONTROL DEVICE

(75) Inventor: Edward Draper, Buckinghamshire (GB)

(73) Assignee: MOXIMED, INC., Hayward, CA (US)

( * ) Notice: Subject to any disclaimer, the term of this patent is extended or adjusted under 35 U.S.C. 154(b) by 372 days.

(21) Appl. No.: 12/628,866

(22) Filed: Dec. 1, 2009

(65) Prior Publication Data
US 2010/0145336 A1 Jun. 10, 2010

Related U.S. Application Data

(60) Continuation of application No. 12/425,969, filed on Apr. 17, 2009, now Pat. No. 9,610,103, which is a
(Continued)

(30) Foreign Application Priority Data

Mar. 28, 2001 (GB) .................................. 0107708.0

(51) Int. Cl.
*A61B 17/00* (2006.01)
*A61B 17/64* (2006.01)
*A61B 17/60* (2006.01)

(52) U.S. Cl.
CPC ...... *A61B 17/6425* (2013.01); *A61B 17/6416* (2013.01); *A61B 17/6441* (2013.01); *A61B 2017/606* (2013.01)

(58) Field of Classification Search
CPC .............. A61B 17/562; A61B 17/6416; A61B 17/6425; A61B 17/6491; A61B 17/7046
(Continued)

(56) References Cited

U.S. PATENT DOCUMENTS

| 2,632,440 A | 3/1953 | Hauser |
| 2,877,033 A | 3/1959 | Koetke |

(Continued)

FOREIGN PATENT DOCUMENTS

| CA | 1205602 | 6/1986 |
| DE | 19855254 | 6/2000 |

(Continued)

OTHER PUBLICATIONS

Yamamoto, Ei et al.; "Effects of Stress Shielding on the Transverse Mechanical Properties of Rabbit Patellar Tendons"; Journal of Biomechanical Engineering, 2000, vol. 122, pp. 608-614.
(Continued)

*Primary Examiner* — Ellen C Hammond
(74) *Attorney, Agent, or Firm* — Cermak Nakajima & McGowan LLP; Adam J. Cermak (57) ABSTRACT

A load control device can be attached to bones on either side of an articulated joint in order to control the forces and loads experienced by the joint. The device comprises an apparatus for controlling the load on articular cartilage of a human or animal joint and includes: a first fixation assembly for attachment to a first bone; a second fixation assembly for attachment to a second bone; a link assembly coupled to the first fixation assembly by a first pivot and coupled to the second fixation assembly by a second pivot, the first and second fixation assembly thereby each being angularly displaceable relative to the link assembly. The apparatus enables a clinician to effectively control the environment of cartilage in a joint during a treatment episode.

13 Claims, 7 Drawing Sheets

Related U.S. Application Data division of application No. 10/675,855, filed on Sep. 25, 2003, now Pat. No. 7,763,020, which is a continuation of application No. PCT/GB02/00844, filed on Feb. 27, 2002.

(58) Field of Classification Search
USPC ..................... 606/53–60, 246–263
See application file for complete search history.

(56) References Cited

U.S. PATENT DOCUMENTS

| | | | |
|---|---|---|---|
| 3,242,922 A | 3/1966 | Thomas | |
| 3,648,294 A | 3/1972 | Shahrestani | |
| 3,681,786 A | 8/1972 | Lynch | |
| 3,779,654 A | 12/1973 | Home | |
| 3,875,594 A | 4/1975 | Lynch | |
| 3,902,482 A | 9/1975 | Taylor | |
| 3,976,061 A | 8/1976 | Volkov et al. | |
| 3,985,127 A | 10/1976 | Volkov et al. | |
| 3,988,783 A | 11/1976 | Treace | |
| 4,187,841 A | 2/1980 | Knutson | |
| 4,246,660 A | 1/1981 | Wevers | |
| 4,308,863 A | 1/1982 | Fischer | |
| 4,353,361 A | 10/1982 | Foster | |
| 4,488,542 A * | 12/1984 | Helland | 606/59 |
| 4,501,266 A | 2/1985 | McDaniel | |
| 4,570,625 A | 2/1986 | Harris | |
| 4,576,158 A | 3/1986 | Boland | |
| 4,621,627 A | 11/1986 | DeBastiani et al. | |
| 4,628,922 A | 12/1986 | Dewar | |
| 4,637,382 A * | 1/1987 | Walker | 606/55 |
| 4,696,293 A * | 9/1987 | Ciullo | 606/57 |
| 4,759,765 A | 7/1988 | Van Kampen | |
| 4,776,851 A | 10/1988 | Bruchman et al. | |
| 4,846,842 A | 7/1989 | Connolly et al. | |
| 4,871,367 A | 10/1989 | Christensen et al. | |
| 4,883,486 A | 11/1989 | Kapadia et al. | |
| 4,919,119 A * | 4/1990 | Jonsson et al. | 606/54 |
| 4,923,471 A | 5/1990 | Morgan | |
| 4,942,875 A | 7/1990 | Hlavacek et al. | |
| 4,947,835 A * | 8/1990 | Hepburn et al. | 602/16 |
| 4,988,349 A | 1/1991 | Pennig | |
| 5,002,574 A | 3/1991 | May et al. | |
| 5,011,497 A | 4/1991 | Persson et al. | |
| 5,019,077 A | 5/1991 | De Bastiani et al. | |
| 5,026,372 A | 6/1991 | Sturtzkopf et al. | |
| 5,041,112 A | 8/1991 | Mingozzi et al. | |
| 5,092,867 A * | 3/1992 | Harms et al. | 606/252 |
| 5,100,403 A | 3/1992 | Hotchkiss et al. | |
| 5,103,811 A | 4/1992 | Crupi | |
| 5,121,742 A | 6/1992 | Engen | |
| 5,122,140 A * | 6/1992 | Asche et al. | 606/55 |
| 5,152,280 A | 10/1992 | Danieli | |
| 5,207,676 A | 5/1993 | Canadell et al. | |
| 5,352,190 A | 10/1994 | Fischer | |
| 5,352,224 A * | 10/1994 | Westermann | 606/286 |
| 5,375,823 A | 12/1994 | Navas | |
| 5,405,347 A | 4/1995 | Lee et al. | |
| 5,415,661 A | 5/1995 | Holmes | |
| 5,456,733 A | 10/1995 | Mcleod et al. | |
| 5,540,688 A | 7/1996 | Navas | |
| 5,575,819 A | 11/1996 | Amis | |
| 5,578,038 A | 11/1996 | Slocum | |
| 5,624,440 A | 4/1997 | Huebner | |
| 5,662,648 A | 9/1997 | Faccioli et al. | |
| 5,662,650 A | 9/1997 | Bailey et al. | |
| 5,695,496 A | 9/1997 | Orsak et al. | |
| 5,681,313 A | 10/1997 | Diez | |
| 5,733,284 A * | 3/1998 | Martin | 606/248 |
| 5,803,924 A | 9/1998 | Oni et al. | |
| 5,873,843 A | 2/1999 | Draper | |
| 5,928,234 A | 7/1999 | Manspeizer | |
| 5,944,719 A | 8/1999 | Leban | |
| 5,976,125 A | 11/1999 | Graham | |
| 5,976,136 A | 11/1999 | Bailey et al. | |
| 6,036,691 A | 3/2000 | Richardson | |
| 6,113,637 A | 9/2000 | Gill et al. | |
| 6,162,223 A * | 12/2000 | Orsak et al. | 606/59 |
| 6,176,860 B1 | 1/2001 | Howard | |
| 6,193,225 B1 | 2/2001 | Watanabe | |
| 6,203,548 B1 | 3/2001 | Helland | |
| 6,248,106 B1 * | 6/2001 | Ferree | 606/263 |
| 6,264,696 B1 | 7/2001 | Reigner et al. | |
| 6,273,914 B1 * | 8/2001 | Papas | 623/17.11 |
| 6,277,124 B1 | 8/2001 | Haag | |
| 6,355,037 B1 | 3/2002 | Crosslin et al. | |
| 6,409,729 B1 | 6/2002 | Martinelli et al. | |
| 6,482,232 B1 | 11/2002 | Boucher et al. | |
| 6,494,914 B2 | 12/2002 | Brown et al. | |
| 6,527,733 B1 | 3/2003 | Ceriani et al. | |
| 6,540,708 B1 * | 4/2003 | Manspeizer | 602/16 |
| 6,572,653 B1 | 6/2003 | Simonson | |
| 6,626,909 B2 * | 9/2003 | Chin | 606/276 |
| 6,663,631 B2 | 12/2003 | Kuntz | |
| 6,692,495 B1 * | 2/2004 | Zacouto | 606/247 |
| 6,752,831 B2 | 6/2004 | Sybert et al. | |
| 6,966,910 B2 | 11/2005 | Ritland | |
| 6,972,020 B1 | 12/2005 | Grayson et al. | |
| 7,029,475 B2 | 4/2006 | Pajabi | |
| 7,141,073 B2 | 11/2006 | May et al. | |
| 7,188,626 B2 | 3/2007 | Foley et al. | |
| 7,201,728 B2 | 4/2007 | Sterling | |
| 7,235,102 B2 | 6/2007 | Ferree et al. | |
| 7,241,298 B2 | 7/2007 | Nemec et al. | |
| 7,252,670 B2 | 8/2007 | Morrison et al. | |
| 7,261,739 B2 | 8/2007 | Ralph et al. | |
| 7,282,052 B2 | 10/2007 | Mullaney | |
| 7,282,065 B2 | 10/2007 | Kirschman | |
| 7,291,150 B2 | 11/2007 | Graf | |
| 7,306,605 B2 | 12/2007 | Ross | |
| 7,361,196 B2 | 4/2008 | Fallin | |
| 8,409,281 B2 * | 4/2013 | Makower et al. | 623/13.12 |
| 2001/0020143 A1 | 9/2001 | Stark et al. | |
| 2002/0029039 A1 * | 3/2002 | Zucherman et al. | 606/61 |
| 2002/0095154 A1 | 7/2002 | Atkinson et al. | |
| 2002/0107524 A1 * | 8/2002 | Magana | 606/103 |
| 2002/0120270 A1 * | 8/2002 | Trieu et al. | 606/61 |
| 2002/0133155 A1 * | 9/2002 | Ferree | 606/61 |
| 2002/0151978 A1 * | 10/2002 | Zacouto et al. | 623/17.12 |
| 2003/0216809 A1 | 11/2003 | Ferguson | |
| 2003/0220643 A1 * | 11/2003 | Ferree | 606/61 |
| 2004/0002708 A1 * | 1/2004 | Ritland | 606/61 |
| 2004/0138659 A1 * | 7/2004 | Austin et al. | 606/54 |
| 2004/0260302 A1 | 12/2004 | Manspeizer | |
| 2004/0267179 A1 | 12/2004 | Leman | |
| 2005/0049708 A1 * | 3/2005 | Atkinson et al. | 623/17.16 |
| 2005/0085754 A1 | 4/2005 | Werding et al. | |
| 2005/0085815 A1 | 4/2005 | Harms et al. | |
| 2005/0119744 A1 | 6/2005 | Buskirk et al. | |
| 2005/0154390 A1 | 7/2005 | Biedermann et al. | |
| 2005/0192674 A1 | 9/2005 | Ferree | |
| 2005/0261680 A1 | 11/2005 | Draper | |
| 2006/0064169 A1 | 3/2006 | Ferree | |
| 2006/0155279 A1 * | 7/2006 | Ogilvie | 606/61 |
| 2006/0178744 A1 | 8/2006 | de Villiers et al. | |
| 2007/0043354 A1 | 2/2007 | Koo et al. | |
| 2007/0043356 A1 | 2/2007 | Timm et al. | |
| 2007/0106299 A1 | 5/2007 | Manspeizer | |
| 2007/0161993 A1 | 7/2007 | Lowery et al. | |
| 2007/0168033 A1 | 7/2007 | Kim et al. | |
| 2007/0168036 A1 | 7/2007 | Ainsworth et al. | |
| 2007/0198088 A1 | 8/2007 | Biedermann et al. | |
| 2007/0198091 A1 | 8/2007 | Boyer et al. | |
| 2007/0244483 A9 | 10/2007 | Winslow et al. | |
| 2007/0244488 A1 | 10/2007 | Metzger et al. | |
| 2007/0288014 A1 | 12/2007 | Shadduck et al. | |
| 2008/0015593 A1 | 1/2008 | Pfefferle et al. | |
| 2008/0071373 A1 | 3/2008 | Molz et al. | |
| 2008/0071375 A1 | 3/2008 | Carver et al. | |
| 2008/0097434 A1 | 4/2008 | Moumene et al. | |

(56) References Cited

U.S. PATENT DOCUMENTS

2008/0097441 A1 4/2008 Hayes et al.
2008/0275571 A1* 11/2008 Clifford et al. ............... 623/46

FOREIGN PATENT DOCUMENTS

| | | |
|---|---|---|
| EP | 0383419 | 8/1990 |
| EP | 0953317 | 4/1999 |
| EP | 1770302 | 4/2007 |
| EP | 1005290 | 2/2008 |
| EP | 1468655 | 5/2008 |
| GB | 1507953 | 4/1978 |
| GB | 2223406 | 4/1990 |
| GB | 2250919 | 10/1993 |
| JP | 59-131348 | 7/1984 |
| JP | 7-100159 | 4/1995 |
| JP | 2532346 | 4/1995 |
| JP | 2000-503865 | 4/2000 |
| JP | 2001-145647 | 4/2000 |
| JP | 2003-102744 | 5/2001 |
| JP | 2006-280951 | 10/2006 |
| JP | 2007-167318 | 7/2007 |
| JP | 2007-167319 | 7/2007 |
| JP | 2007-170969 | 7/2007 |
| RU | 2085148 | 7/1994 |
| RU | 2217105 | 11/2003 |
| RU | 2241400 | 9/2004 |
| SU | 578063 | 11/1977 |
| SU | 578957 | 11/1977 |
| SU | 624613 | 8/1978 |
| SU | 640740 | 1/1979 |
| SU | 704605 | 12/1979 |
| SU | 719612 | 3/1980 |
| SU | 741872 | 7/1980 |
| SU | 1186204 | 10/1985 |
| SU | 1251889 | 8/1986 |
| SU | 1316666 | 6/1987 |
| SU | 1588404 | 8/1990 |
| SU | 1699441 | 12/1991 |
| SU | 1769868 | 10/1992 |
| WO | WO91/07137 | 5/1991 |
| WO | WO94/06364 | 3/1994 |
| WO | WO96/19944 | 7/1996 |
| WO | WO04/019831 | 3/2004 |
| WO | WO04/024037 | 3/2004 |
| WO | WO07/056645 | 5/2005 |
| WO | WO2006/045091 | 4/2006 |
| WO | WO2006/049993 | 5/2006 |
| WO | WO06/110578 | 10/2006 |
| WO | WO07/090009 | 8/2007 |
| WO | WO07/090015 | 8/2007 |
| WO | WO07/090017 | 8/2007 |
| WO | WO2007114769 | 10/2007 |
| WO | WO2007117571 | 10/2007 |
| WO | WO2008006098 | 1/2008 |

OTHER PUBLICATIONS

Tomita, Naohide, "Development of Treatment Devices for Cartilage Regeneration", BME vol. 16, No. 2.
Lentsner, A.A., et al., "Device for Functional Relief of Hip Joint in Cotyloid Cavity Fracture Cases", Ortop Travmatol Protez. Apr. 1999 (4) 44-6.
Nagai, et al., "B109 Mobility Evaluation of Hip-Joint Nonweight-Bearing Device", The Japan Society of Mechanical Engineers No. 02-26.
Lapinskaya, V.S., et al., "An Endoapparatus for Restoration of the Hip Joint", Writers Collective, 2008, UDK 615.472.03:616,728.2-089.28.
Wilkins, Ross M., M.D. et al.; "The Phenix Expandable Prosthesis"; Clinical Orthopaedics and Related Research, No. 382, pp. 51-58.
Weisstein, Jason S., M.D. et al.; "Oncologic Approaches to Pediatric Limb Preservation"; Journal of the American Academy of Orthopaedic Surgeons; vol. 13, No. 8, Dec. 2005.
Uchikura, C. et al.; "Comparative study of nonbridging and bridging external fixators for unstable distal radius fractures"; Journal of Orthopaedic Science, 2004, vol. 9, pp. 560-565.
Sommerkamp, G. et al.; "Dynamic external fixation of unstable reatures of the distal part of the radius"; The Journal of Bone and Joint Surgery; 1994, vol. 76-A, No. 8, pp. 1149-1161.
Madey, S. et al; Hinged external fixation of the elbow: optimal axis alignment to minimize motion resistance; Journal of Orthopaedic Trauma, 2000, vol. 14, No. 1, pp. 41-47.
Neel, Michael D., M.D.; "Repiphysis—Limb Salvage System for the Skeletally Immature"; Wright Medical Techology, Repiphysis Limb Salvage System, 2001, pp. 1-8.
Neel, Michael D. M.D. et al.; "Early Multicenter Experience With a Noninvasive Expandable Prosthesis"; Clinical Orthopaedics and Related Research, 2003, No. 415, pp. 72-81.
Nockels, Russ P.; "Dynamic Stabilization in the Surgical Management of Painful Lumbar Spinal Disorders"; Spine, 2005, vol. 30, No. 16S, pp. S68-S72.
Orthofix; "Xcaliber Articulated Ankle"; advertising brochure, May 2004.
Orthofix; "Gentle Limb Deformity Correction", website pages, http://www.eight-plate.com/, 2008.
Perry, Clayton R. et al.; "Patellar Fixation Protected with a Load-Sharing Cable: A Mechanical and Clinical Study": Journal of Orthopaedic Trauma, 1988, vol. 2, No. 3, pp. 234-240.
Pollo, Fabian E. et al.; "Reduction of Medical Compartment Loads With Valgus Bracing of the Osteoarthritic Knee"; American Journal Sports Medicine, vol. 30, No. 3, 2002; pp. 414-421.
Aldegheri, Roberto, M.D. et al.; "Articulated Distraction of the Hip—Conservative Surgery for Arthritis in Young Patients", Clinical Orthopaedics and Related Research, No. 301, pp. 94-101.
Benzel, Edward; "Qualititive Attributes of Spinal Implants"; in: Biomechanics of Spine Stabilization, 1995.
Buckwalter, Joseph A,: "Joint distraction for osteoarthritis"; The Lancet, Department of Orthopaedic Surgery, University of Iowa Hospitals and Clinics, vol. 347, Feb. 3, 1996, pp. 279-280.
Deie, Masataka, M.D. et al.; "A new Articulated Distraction Arthrosplasty Device for Treatment of the Osteoarthritic Knee Joint: A Preliminary Report"; Arthroscopy: The Journal of Arthoscopic and Related Surgery; vol. 23, No. 8 Aug. 2007: pp. 833-838.
Dienst, M. et al.; "Dynamic external fixation for distal radius fractures"; Clinical Orthopaedics and Related Research, 1997, vol. 338, pp. 160-171.
Hall, J. et al.; "Use of a hinged external fixator for elbow instability after severe distal humeral fracture"; Journal of Orthopaedic Trauma, 2000, vol. 14, No. 6 pp. 442-448.
Klein, D. et al.; "Percutaneous treatment of carpal, metacarpal, and phalangeal injuries"; Clinical Orthopaedics and Related Research, 200, vol. 375, pp. 116-125.
Krakauer, J. et al.; "Hinged device for fractures involving the proximal interphalangeal joint"; Clinical Orthopaedics and Related Research, 1996, vol. 327, pp. 29-37.
Lafeber et al., Unloading Joints to Treat Osteoarthritis, Including Joint Distraction, Current Opinion in Rheumatology 2006, 18; 519-525.
European Search Report for European Patent App. No. 08169426.7 (dated Jul. 22, 2014).
Office Action from pending U.S. Appl. No. 12/425,969 dated Jun. 17, 2016.

* cited by examiner

BONE FIXATED, ARTICULATED JOINT LOAD CONTROL DEVICE

CROSS REFERENCE TO RELATED APPLICATIONS

This application is a continuation of, and claims priority under 35 U.S.C. § 120 to, U.S. application Ser. No. 12/425,969, filed on Apr. 17, 2009, now U.S. Pat. No. 9,610,103, issued on Apr. 4, 2017, which is a divisional of and claimed priority under 35 U.S.C. § 120 to U.S. application Ser. No. 10/675,855, filed on Sep. 25, 2003, now U.S. Pat. No. 7,763,020, issued on Jul. 27, 2010, which was a continuation of, and claimed priority under 35 U.S.C. § 120 to, PCT Patent App. No. PCT/GB02/00844, filed Feb. 27, 2002, which claimed benefit under 35 U.S.C. § 119 to British Patent App. No. 0107708.0, filed Mar. 28, 2001, the entire disclosures of which are expressly incorporated herein by reference.

BACKGROUND

The present invention relates to devices for restricting or controlling the movement or loading levels on joints in the human or animal body.

The human or animal body uses articular cartilage to surface many of its joints. This tissue tolerates relatively high levels of compression while having a low coefficient of friction—approximately that of wet ice on wet ice.

Bone, on which the cartilage is supported, is stiffer and stronger. Away from the joints, bone normally forms in large, thick-walled tubes. However, under the cartilage at the joints, the bone forms a three dimensional mesh of so called "cancellous" bone. Cancellous bone is more compliant than the rest of the bone structure and helps spread the load that the cartilage experiences, thus reducing the peak stresses on the cartilage.

Both cartilage and bone are living tissues that respond and adapt to the loads they experience. There is strong evidence that the loads that joint surfaces experience can be categorised into four regions or "loading zones".

1. Under-Loading Zone.

If a joint surface remains unloaded for appreciable periods of time the cartilage tends to soften and weaken.

2. Healthy Zone.

Joint surfaces can and do last a lifetime and if they experience healthy levels of load they can be considered to effectively last indefinitely.

3. Tolerant Zone.

As with engineering materials that experience structural loads, both bone and cartilage begin to show signs of failure at loads that are below their ultimate strength. Unlike engineering materials, however, cartilage and bone have some ability to repair themselves, bone more so. There are levels of loading that will cause micro-structural problems and trigger the repair processes. The body can tolerate these load levels as long as it has time to recuperate.

4. Overloaded Zone.

There comes a level of load at which the skeleton will fail catastrophically. If the load level on a joint surface reaches this level even once then there will be severe consequences.

One of the major consequences of excessive loading is osteoarthritis. This loading could be either from a single overload in the overloaded zone or from loading within the tolerant zone too frequently.

The picture of safe joint loading is further complicated by the cascade of events that occur during the onset of osteoarthritis. These events include the break up of the cartilage, and bone 'sclerosis' in which the bone becomes denser and stiffer. This means that the maximum level of loading that can be considered healthy or tolerated falls, almost certainly to levels below that experienced in walking and standing.

Newly implanted grafts or tissue-engineered constructs will also have lower tolerance limits while they are establishing themselves within the joint.

In fact the treatment of osteoarthritis and other conditions is severely hampered when a surgeon is not able to control and prescribe the levels of joint load. Furthermore, bone healing research has shown that some mechanical stimulation can enhance the healing response and it is likely that the optimum regime for a cartilage/bone graft or construct will involve different levels of load over time, eg. during a particular treatment schedule.

There is a need for a device that will facilitate the control of load on a joint undergoing treatment or therapy, to enable use of the joint within the healthy loading zone, or even within the healthy and tolerant loading zones, during the treatment episode.

There is further need for a device to preferably provide such control while allowing full, or relatively full mobility of a patient undergoing the treatment.

Such devices would be desirable particularly during the early treatment of, for example, an osteoarthritic joint. Under an appropriate treatment regime providing controlled loading, the condition of the joint may improve, possibly back to full health.

In the prior art, existing load controlling regimes and devices for use in treatment or therapy of articulating joints include the following.

a) Bed-rest or isolation of a joint is possible but, as indicated above, the long-term consequences of applying no load or generally maintaining the joint in the underloaded zone are not good.

b) Passive movement of a joint has been tried with some success. During this treatment, movement is applied to the joint by an external device while the joint is rested. However, this does not give the opportunity to vary the load levels on the joint, eg. to work the joint within the healthy zone for that joint at any given stage of the treatment program.

c) Traction across a joint has long been used to counteract the compressive loads normally experienced by the joint. This is done either in bed or using an external fixator. Fixators exist which not only apply traction, but also have simple hinges to allow some joint motion.

d) External braces have been used to apply a bending moment across the joint and at 90.degree. to the motion to move the centre of pressure from one part of the joint to another. However, since these braces are not attached directly to the skeleton, control of the applied loads is poor.

According to one aspect, the present invention provides an apparatus for controlling the load on articular cartilage of a human or animal joint comprising:

a first fixation assembly for attachment to a first bone;

a second fixation assembly for attachment to a second bone; and a link assembly coupled to the first fixation assembly by a first pivot and coupled to the second fixation assembly by a second pivot, the first and second fixation assembly thereby each being angularly displaceable relative to the link assembly.

According to another aspect, the present invention provides a method of controlling loading on a joint comprising the steps of:

attaching a first fixation assembly to a first bone;

attaching a second fixation assembly to a second bone, the second bone being connected to the second bone by an articulating joint;

coupling said first fixation assembly and said second fixation assembly by way of a link assembly so that said first fixation assembly and said second fixation assembly are each angularly displaceable relative to the link assembly.

DETAILED DESCRIPTION

Figure 1:
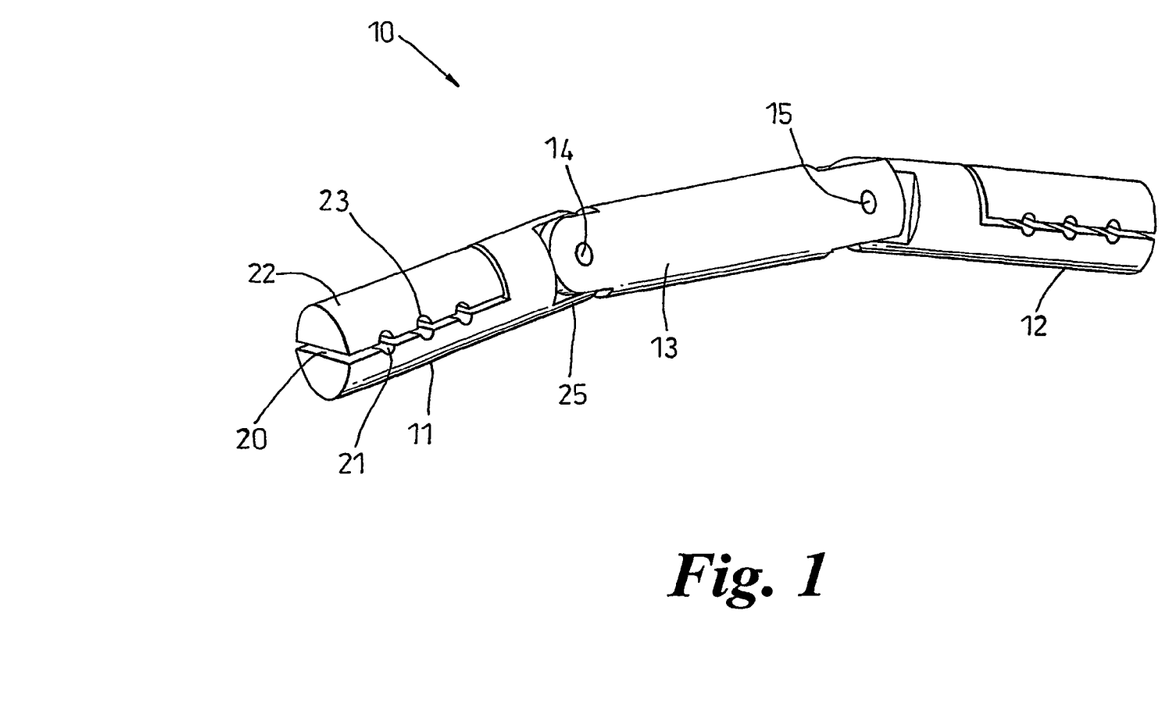
FIG. 1 shows a perspective view of a fixator for controlling loads on articular cartilage according to a preferred embodiment of the present invention.

With reference to FIG. 1, there is shown an articulated joint load controlling device or fixator 10 according to one embodiment of the invention. The fixator 10 comprises a first fixation assembly 11, a second fixation assembly 12 and a link assembly 13 connecting the first and second fixation assemblies 11, 12.

The first and second fixation assemblies 11, 12 are each coupled to the link assembly 13 by a pivot 14, 15 or other equivalent means facilitating angular displacement of the respective fixation assembly to the link assembly. Throughout the present specification, use of the word "pivot" is intended to encompass all such equivalent means for facilitating angular displacement. It will be understood that the first and second fixation assemblies 11, 12 are therefore not only angularly displaceable relative to one another, but are also capable of some relative translational movement subject to the geometric limitations provided by the link assembly 13.

Preferably, the axes of the pivots 14, 15 are parallel so that the first and second fixation assemblies 11, 12 will rotate about the link assembly in the same plane.

In an alternative embodiment, however, the pivots 14 and 15 might not be axially parallel, in order to better follow the three-dimensional movement of a particular joint. In a further embodiment, one or both pivots 14, 15 might be of the universal joint type, such that the pivot allows two degrees of rotational freedom rather than only a single degree of rotational freedom, in order to better follow the three-dimensional movement of, for example, a ball joint.

Each fixation assembly 11, 12 preferably comprises a faceplate 20 having one or more slots 21 defined in the faceplate surface. Coupled to the faceplate 20 is a clamp plate 22 which may be tightened onto the faceplate 20 by way of screws, or other means known in the art. Preferably, the clamp plate includes corresponding slots 23. As shown more clearly in FIG. 2, the face plate 20 and clamp plate 22 together provide an anchorage for one or more bone pins 30 which can be screwed into or otherwise fixed to a bone using known techniques. Other examples of fixation assemblies are illustrated later in connection with FIG. 5.

In the arrangement of FIG. 1, a single load controlling fixator 10 may be attached to an articulating joint by way of first bone pins 30 screwed into one side of a first bone using the first fixation assembly 11, and second bone pins 30 screwed into a corresponding side of a second bone using the second fixation assembly 12. The first and second bones are on either side of an articulating joint to be controlled by the fixator.

Figure 2:
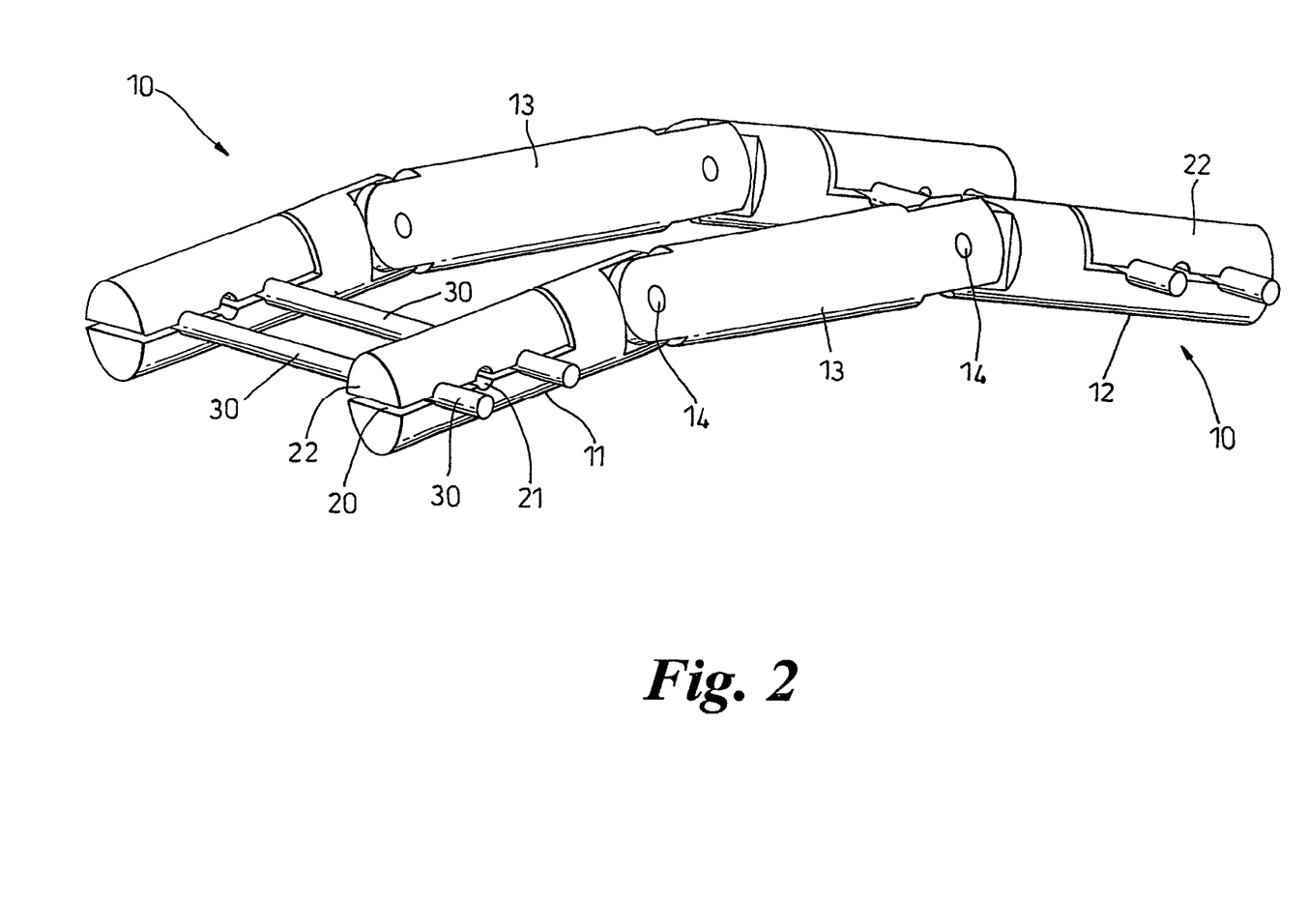
FIG. 2 shows a perspective view of a pair of fixators of FIG. 2 in a dual sided or bilateral configuration.

In the arrangement of FIG. 2, two load controlling devices or fixators may be used in a bilateral configuration on either side of an articulating joint, the bone pins 30 passing right through the respective first and second bones on either side of the articulating joint. By applying compression in one fixator and tension in the other fixator, it is possible to apply a bending moment to the joint so as to move the centre of pressure within the joint in a controlled manner and so relieve the loads experienced by the areas of concern.

Figure 7:
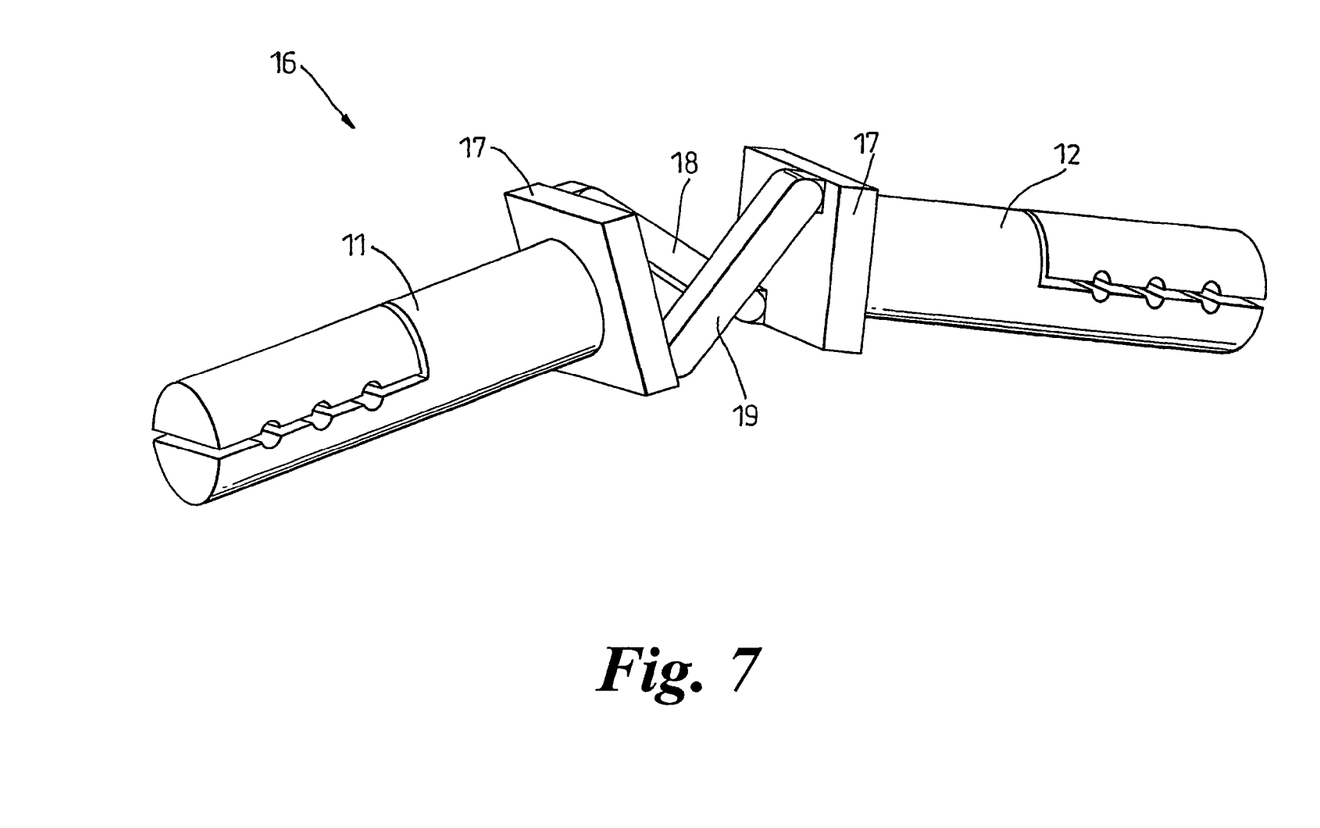
FIG. 7 shows a parallel-crosswise configuration of link assembly.

In further embodiments, first and second fixation assemblies 11, 12 of a fixator 10 might be coupled to two or more link assemblies in series or in parallel with one another. For example, as shown in FIG. 7, a fixator 16 comprises a first fixation assembly 11 and a second fixation assembly 12 that are connected by a link assembly that comprises a pair of link members 18, 19 in a parallel-crosswise configuration. Each link member is pivotally anchored to both the first and second fixation assemblies 11, 12 by way of face plates 17, the link members being laterally displaced from one another. In the embodiment shown, the link member 18 and link member 19 are not only laterally displaced from one another, but also angularly displaced from one another, in a crosswise formation. This arrangement provides a controlled, limited degree of freedom of relative movement of the first and second fixation assemblies. By adjusting the position of the two link members it is possible to mimic the movement of the knee.

Referring now to FIG. 3, various arrangements of link assemblies and their respective functions will now be described.

Figures 3A, 3B, 3C:
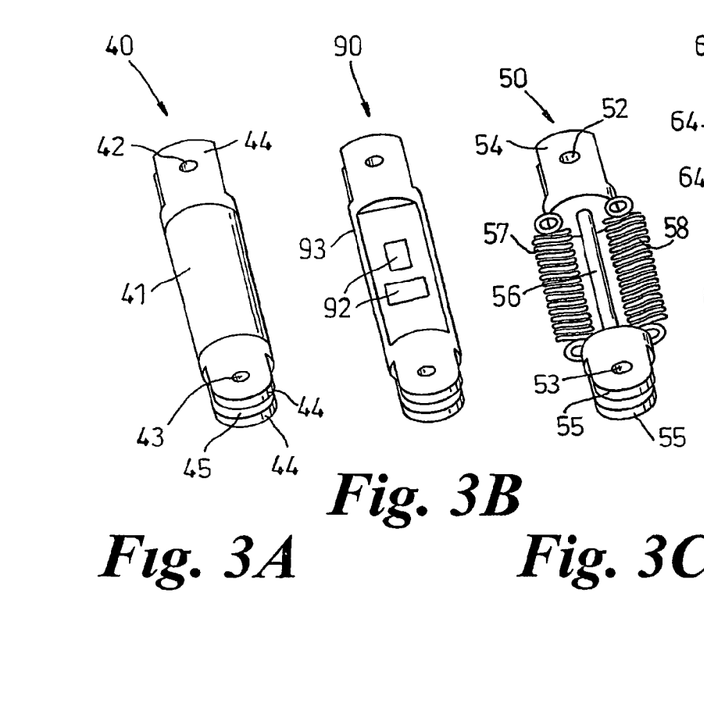
FIG. 3 shows perspective views of a selection of central modules suitable for use with the fixators of FIGS. 1 and 2.

In a first arrangement, labelled FIG. 3A, the link assembly 40 comprises a rigid, fixed length member having a barrel centre section 41 and a pair of lugs 44 extending from each end. Each pair of lugs 44 includes a pair of coaxial apertures or hubs 42, 43 in which can rotate respective pivot pins 14, 15 (FIG. 1). Each pair of lugs 44 define therebetween a slot 45 adapted to receive a corresponding lug 25 (see FIG. 1) of a respective fixation assembly 11 or 12. The link assembly 40 essentially maintains first and second pivots 14 and 15 at a fixed distance of separation.

In a further embodiment, the lug pairs 44 and barrel centre section 41 may be screwed together for quick disassembly and re-assembly, enabling different length barrel centre sections 41 to readily be used to provide a link assembly 40 of an appropriate length to the joint under treatment or therapy and to be changed during a treatment program.

In another arrangement, labelled FIG. 3C, a link assembly 50 provides for a variable distance of separation of pivots 14, 15 in hubs 52, 53. Link assembly 50 comprises a pair of lugs 54 and a pair of lugs 55, each pair being mounted on a central shaft 56 and being axially displaceable therealong. A pair of tension springs 57, 58 provide a means for biasing the distance of separation of the pivots 14, 15 towards a minimum limit of separation of the lug pairs 54, 55 to apply greater compression forces than those normally experienced by the joint.

Figures 3D, 3E:
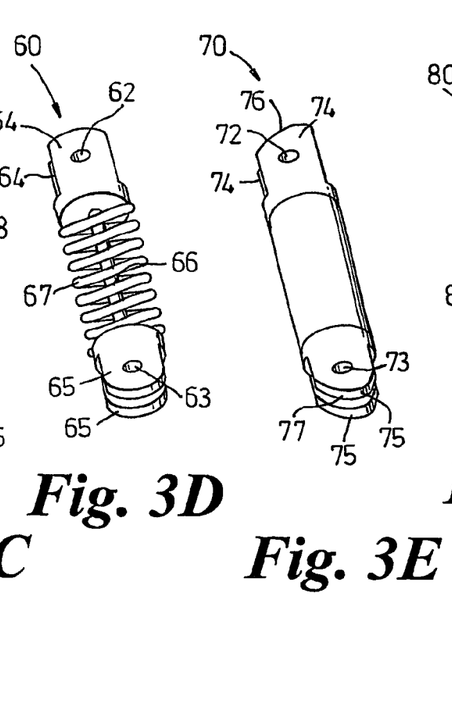

In another arrangement, labelled FIG. 3D, a link assembly 60 provides for a variable distance of separation of pivots 14, 15 in hubs 62, 63. Link assembly 60 comprises a pair of lugs 64 and a pair of lugs 65, each pair being mounted on a central shaft 66 and being axially displaceable therealong. A compression spring 67 provides a means for biasing the distance of separation of the pivots 14, 15 towards a maximum limit of separation of the lug pairs 64, 65 so as to counteract the natural compressive forces experienced by the joint.

It will be understood that the functions of link assembly 50 and link assembly 60 may be combined to provide bias towards a central position so that there is resistance against movement of the pairs of lugs from a centre position. More generally, this provides means for biasing the first and second pivots towards an intermediate distance of separation between predetermined limits of separation of the lug pairs 54, 55 or 64, 65.

Although not shown in FIG. 3C or 3D, it is also possible to provide a locking member which is axially adjustable along the length of the link assembly to adjust the limit or limits of separation of the lug pairs. The locking member could be provided, for example, by way of a screw-threaded collar on the central shaft 56 or 66 using techniques that will be understood by those skilled in the art.

Figure 3F:
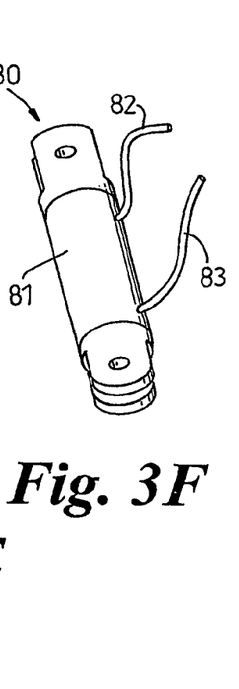

In another arrangement, labelled as FIG. 3F, the provision of a means for controlling the distance of separation of pivots 14, 15 could be by way of a link assembly 80 that includes a pneumatic or hydraulic cylinder 81, controlled externally by a controller (not shown) connected thereto by two feed pipes 82, 83. The pneumatic or hydraulic cylinder may also provide means for biasing the distance of separation of the first and second pivots to a predetermined position.

It will be understood that the functions of the pneumatic or hydraulic cylinder 81 could be alternatively provided by an electrically driven system.

In another arrangement, labelled FIG. 3E, the link assembly 70 (which may generally correspond with a links 50 or 60 having variable separation members) may also be provided with a mechanism for varying the distance of separation of the pivots 14, 15 according to the angular displacement of the first and/or second fixation assemblies relative to the link assembly. This would enable, for example, the separation to be increased in the last 5° of angular displacement.

In the preferred embodiment shown, a cam surface 76, 77 is provided on the circumferential edge of one or both of the lug pairs 74, 75 including a pair of coaxial apertures or hubs 72, 73. The cam surface bears on a corresponding bearing surface on a respective fixation assembly 11, 12 and is preferably adapted to vary the separation of the fixation assemblies as a function of the angular displacement. As an example, for a fixator attached to a knee joint, the cam surfaces 76, 77 can be arranged so that as the knee is moved to the fully extended condition, the fixator ensures a greater separation of the fixation assemblies 11, 12 thereby reducing pressure on the joint surfaces.

In another arrangement, the cam surfaces 76, 77 could be adapted to limit the angular displacement of that fixation assembly.

In another arrangement, the cam surfaces may be used to provide a varying degree of resistance to angular displacement of the fixation assembly. More generally, the cam surface may be adapted to provide a means for progressively increasing resistance to angular displacement of the fixation assembly relative to the link assembly as a function of the angular displacement from a reference position.

The means for limiting angular displacement could alternatively be provided by a stepped surface on the circumferential edge of the lug in a manner which will be understood by those skilled in the art.

In conjunction with any of the link assemblies described above, a link assembly 90 as shown in FIG. 3B may be provided with means for recording loads applied across the link assembly. The sensor may be adapted to monitor any one or more of the tensile load, the compression load, shear forces or bending forces applied across the link assembly. Preferably the sensor comprises a strain gauge. Such a device makes it possible to determine the load actually being carried by a joint. In the preferred embodiment shown, this is achieved by the installation of strain gauges 92 into the barrel 93 of the link assembly 90.

Separate transducers could be added to monitor angular displacement of the fixation assemblies relative to the link assembly 90.

Figure 4:
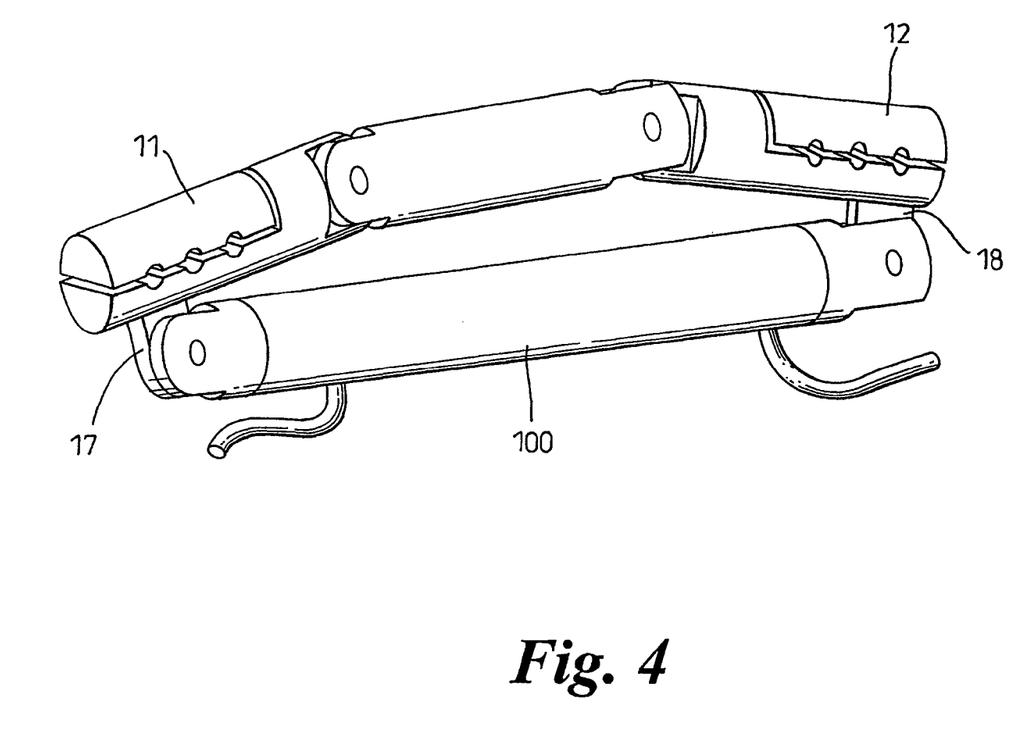
FIG. 4 shows a perspective view of an externally powered fixator.

In another arrangement, as shown in FIG. 4, the angular displacement of the fixation assemblies relative to one another may be controlled externally. This can be achieved by a linear actuator 100 linked to the first and second fixation assemblies 11, 12 by way of brackets 17, 18 each extending from a respective fixation assembly in a direction orthogonal to the pivot axis.

The linear actuator 100 may be powered electrically, pneumatically or hydraulically and enables movement of a joint to be automatically controlled for exercise within the healthy load zone without use of the associated musculature.

Figure 6:
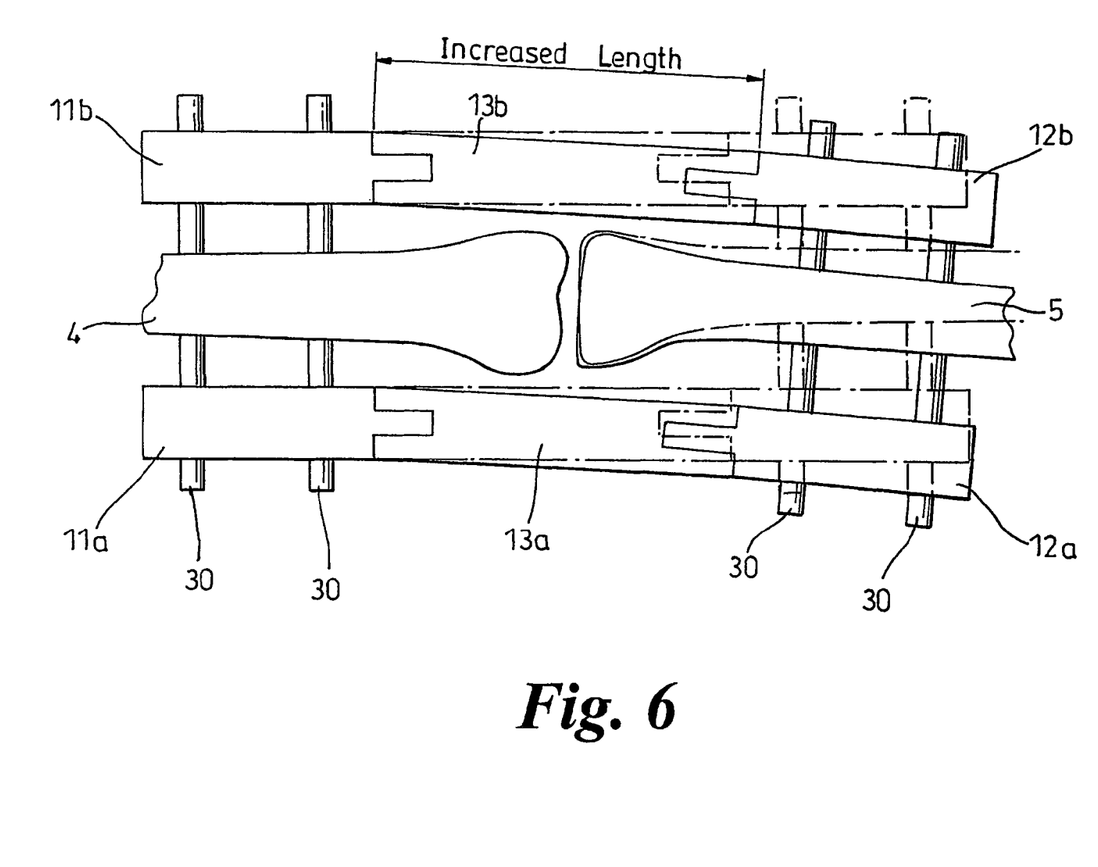
FIG. 6 shows a plan view of a bilateral configuration of fixators as in FIG. 2, illustrating the effects of unilateral variation in the length of link assembly.

Referring back to FIG. 2, it will be noted that when the various link assemblies described in connection with FIG. 3 are used in the bilateral configuration, it is possible, by varying the length of the link assembly 13 independently on either side of the joint, to alter the position of the centre of pressure in the joint. This can be particularly useful in the treatment of knees. An example of the effects of this is illustrated in FIG. 6. In the figure, a bilateral configuration of fixation assemblies is shown similar to that of FIG. 2, viewed from above (ie. generally perpendicular to the pivot axes). In this example, fixation assemblies 11a, 12a and 111b, 12b are respectively connected by link assemblies 13a, 13b. A unilateral adjustment of the length of link assembly 13b results in a relative angular displacement of the bones 4, 5 that varies with articulation of the bones about the axis of the joint, thereby imposing an angulation on the joint. This will tend to have the effect of reducing the load experienced at the joint surface on the side nearest to the lengthened segment.

Figure 5A:
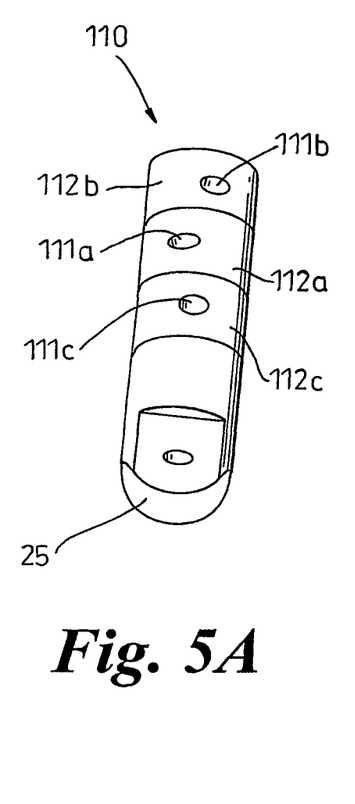
FIG. 5 shows perspective views of a selection of alternative fixation assemblies suitable for use in the fixators of FIGS. 1 and 2.

With reference to FIG. 5, alternative arrangements of fixation assemblies which themselves facilitate further angular degrees of freedom of the fixator are now described. FIG. 5A shows a fixation assembly 110 have a lug 25 for attachment to the various possible link assemblies 13, 40, 50, 60, 70, 80, 90. The body of the fixation assembly includes a plurality of apertures 111a, 111b, 111c each adapted to receive a bone pin 30. In this arrangement, however, each aperture is defined in a corresponding rotatable collar 112a, 112b, 112c such that the angles of the bone pins 30 may be varied on and about the central longitudinal axis of the fixation assembly 110.

Figure 5B:
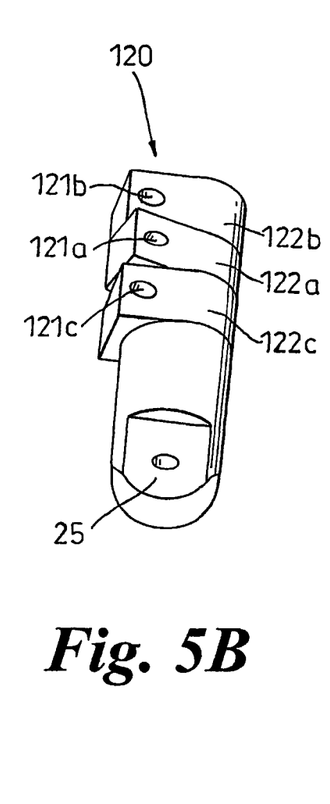

The fixation assembly 120 as shown in FIG. 5b is similar to that of FIG. 5a, except that in this case the apertures 121a, 121b, 121c are laterally offset from the central longitudinal axis of the fixation assembly. Each aperture is again defined in a corresponding rotatable collar 122*a*, 122*b*, 122*c* so that the angles of the bone pins 30 may be varied about a longitudinal axis that is laterally displaced from the central longitudinal axis of the fixation assembly 120.

Figure 5C:
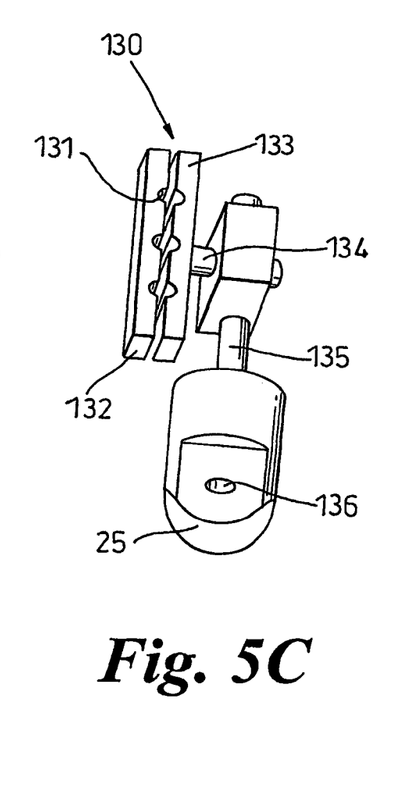

The fixation assembly 130 as shown in FIG. 5*c* provides a further degree of freedom. In this arrangement, bone pins 30 are located in slots 131 formed between a first clamp plate 132 and a second clamp plate 133. The clamp plates 132, 133 are rotatable about a first axis (transverse to a longitudinal axis of the fixation assembly 130) on pivot 134, and about a second axis (preferably a longitudinal axis of the fixation assembly 130) on pivot 135. Taken together with the pivot through aperture 136, this provides a full three rotational degrees of freedom of the bone relative to a link assembly.

The fixator device embodiments as generally described above therefore provide a means for applying and/or limiting tension, compression, torsion, bending and shear forces to an articulated joint in a controlled manner and provide for some or all of the following treatment regimes either in isolation or in any combination. Also it will be possible to change the regime or combination of regimes easily and without the need for a sterile environment or anaesthesia. It is noted that joints of the skeleton naturally experience compression and the fixators of the present invention can provide amelioration of this by applying tension.

1. Continuous Traction.

The level of tension can be varied according to the length of the link assembly used and this can be further varied according to the bias strengths applied by the springs 57, 58, 67.

2. Partial or Full Support.

Some or all of the compression that would otherwise be carried by the joint may be taken by the device, and this can be a function of the angle of support by control of spring strength and angle of fixation to the bones.

3. Application of a Bending Moment, Torsion or Shear Force.

Application of these loads to the joint allows the clinician to move the centre of pressure within the joint to regions that are healthy.

4. Application of an Externally Powered Loading Regime.

This can occur normally while the subject is at rest at set angles, load levels, loading and unloading rates and frequencies using the powered embodiments described above. Providing a portable power supply will, however, allow the patient to continue to move freely.

5. Allowing the Joint Load to be Gradually Increased.

This may be desirable at the end of a treatment episode. This can be done either by applying additional compression or a bending moment, shear force or torsion in the opposite direction from that described above.

6. Load Measurement.

The device as described in connection with FIG. 3B allows the clinician to detect and record the loads experienced across a joint, and also the load applied across the joint by the device.

The motive forces applied across the joints may be from normal physiological loads of the musculoskeletal system or from an externally applied source such as described with reference to FIG. 4.

It will be noted that the preferred design of the devices described above enable the link assemblies and fixation assemblies to be readily disconnected from the bone pins 30 in order to replace or adjust the devices during a treatment schedule. Still further, in the preferred designs, the link assemblies may be adjusted in situ. Preferably, the devices will be able to be removed in their entirety within an outpatient clinic.

The articulated joint controlling devices of the present invention can be used in the treatment not only of rheumatoid arthritis, but for the treatment of many other conditions such as articular fractures, and following surgical procedures such as osteochondral transfers and joint surface replacement with cartilage graft.

Other embodiments are within the scope of the appended claims.

What is claimed:

1. An apparatus for controlling the load on articular cartilage of a human or animal joint comprising:
    a first fixation assembly configured for rigid attachment to a first bone;
    a second fixation assembly configured for rigid attachment to a second bone; and
    a link assembly coupled to the first and second fixation assemblies, the link assembly including
        a first pivot connected to the first fixation assembly,
        a second pivot connected to the second fixation assembly, and
        a set of two parallel helical springs,
    wherein the link assembly is configured to permit full mobility of the joint in three perpendicular planes.

2. The apparatus of claim 1, wherein the first and second fixation assembly are each angularly displaceable relative to the link assembly.

3. The apparatus of claim 1, wherein the first and second pivots provide at least two degrees of rotational freedom.

4. The apparatus of claim 3, wherein the first and second pivots are universal joints.

5. The apparatus of claim 4, wherein the universal joints are ball joints.

6. The apparatus of claim 1, wherein the link assembly varies a distance of separation of the pivots according to the angular displacement of the joint.

7. The apparatus of claim 6, wherein the separation is increased in the last 5° of angular displacement.

8. The apparatus of claim 1, wherein the link assembly includes a variable separation member for permitting the first and second pivots to vary in their distance of separation.

9. The apparatus of claim 8, wherein the variable separation member controllably varies the distance of separation of the first and second pivots.

10. The apparatus of claim 1, wherein the first and second fixation assemblies are configured to be fixed to first and second bones of a knee joint.

11. The apparatus of claim 1, wherein the set of two parallel springs are arranged side by side in the same link assembly.

12. The apparatus of claim 1, wherein the link assembly further comprises a pair of lugs and an axial shaft extending between the lugs, wherein at least one of the lugs is axially displaceable with respect to the axial shaft.

13. The apparatus of claim 12, wherein the lugs are connected to the first and second fixation assemblies by the first and second pivots.

* * * * *